(12) United States Patent
Rabasco et al.

(10) Patent No.: US 6,458,876 B1
(45) Date of Patent: Oct. 1, 2002

(54) INK JET PAPER COATINGS CONTAINING POLYVINYL ALCOHOL-ALKYLATED POLYAMINE BLENDS

(75) Inventors: John Joseph Rabasco; Kevin Rodney Lassila, both of Macungie; Richard Van Court Carr; Kristen Elaine Minnich, both of Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/370,802

(22) Filed: Aug. 9, 1999

(51) Int. Cl.[7] ............................. C08K 3/36; C08K 5/17
(52) U.S. Cl. ................. 524/253; 524/425; 524/437; 524/445; 524/451; 524/492; 524/493
(58) Field of Search .................. 524/253, 493, 524/492, 425, 437, 445, 451

(56) References Cited

U.S. PATENT DOCUMENTS

| | | | |
|---|---|---|---|
| 2,267,205 A | 12/1941 | Kyrides | 252/152 |
| 4,120,979 A | * 10/1978 | Schwarzmann et al. | 424/325 |
| 4,195,152 A | 3/1980 | Floyd | 528/87 |
| 4,368,053 A | * 1/1983 | Eckhardt et al. | 8/102 |
| 4,944,988 A | 7/1990 | Yasuda et al. | 428/195 |
| 4,983,263 A | * 1/1991 | Yasuda et al. | 204/44.2 |
| 5,270,103 A | 12/1993 | Oliver et al. | 428/219 |
| 5,660,622 A | * 8/1997 | Nikoloff | 106/287.34 |
| 5,804,640 A | 9/1998 | Laura et al. | 524/507 |
| 5,853,899 A | * 12/1998 | Anderson et al. | 428/507 |
| 5,965,244 A | * 10/1999 | Tang et al. | 428/195 |
| 6,015,852 A | * 1/2000 | Lassila et al. | 524/251 |

FOREIGN PATENT DOCUMENTS

| | | |
|---|---|---|
| EP | 0754560 | 1/1997 |
| EP | 0899286 | 3/1999 |
| EP | 0916392 | 5/1999 |
| EP | 0921164 | 6/1999 |
| JP | 63049478 | 3/1988 |
| JP | 63160875 | 7/1988 |
| JP | 63162276 | 7/1988 |
| JP | 01186372 | 7/1989 |
| JP | 01283182 | 11/1989 |
| JP | 59096907 | 9/1993 |
| JP | 06143800 | 5/1994 |
| JP | 06247036 | 9/1994 |
| JP | 06297833 | 10/1994 |

OTHER PUBLICATIONS

Murata, Yoshifumi; and Michihiro Ueda, "Antimicrobial Property of N–Alkyldiethylenetriamines and N–acyldiethylenetriamines against Some Dental Plaque Bacteria", 1989 Soc. Antibac. Antifung. Agents, Jpn., vo. 17, No. 8 pp 7–11.

* cited by examiner

Primary Examiner—Judy M. Reddick
(74) Attorney, Agent, or Firm—Michael Leach

(57) ABSTRACT

Improved ink jet paper coatings which impart high optical density images and excellent water resistance to paper and a process for making an improved ink jet recording paper. The coating composition comprises an inorganic pigment preferably silica, and a PVOH composition in which the PVOH is blended with an alkylated non-polymeric polyamine.

13 Claims, No Drawings

INK JET PAPER COATINGS CONTAINING POLYVINYL ALCOHOL-ALKYLATED POLYAMINE BLENDS

BACKGROUND OF THE INVENTION

Advances in ink jet technology have placed increased demands on recording papers. To function properly, the recording paper must quickly absorb the ink and ink vehicles directly after printing, maximize the ink optical density, minimize bleeding and wicking of the ink, and provide good water and light fastness. To obtain a paper with the above functions, the paper is usually treated with one or more coatings.

Ink jet paper coatings typically comprise silica pigment for its high absorption power and a polymeric binder, such as poly(vinyl alcohol) "PVOH", for its high binding strength. Non-silica pigments, such as clays, calcium carbonate, titanium dioxide, and aluminum hydrate, are also used. Other known polymeric binders include poly(vinylpyrrolidone), styrene-butadiene copolymers, poly(vinyl acetate), starch, and amine functional polymers such as amine functional PVOH.

Most of the commercially available amine functional homo- and copolymers and amine functional PVOHs are economically unattractive. The commercially available amine functional PVOHs, in addition to being costly, also suffer from low levels of amine functionality. As a result of the low levels of amine functionality, these materials fail to meet the stringent performance requirements for good ink jet print quality, especially for the high-end, photographic grade ink jet papers. The printed image density and sharpness are inadequate, as is the water and light resistance. There has, therefore, been a continuing need to produce a higher performing polymeric system that will provide good printed image density and sharpness as well as water and light resistance.

Much of the prior art addresses these performance issues by blending various synthetic amine-containing polymers or copolymers into ink jet coating compositions. The ratios of amine containing polymers or copolymers, PVOH binder, pigment, and other additives, are then varied to achieve the desired final ink jet paper properties.

However, compatibility problems can arise using such blends. For example: 1) when the ink jet coating composition is prepared and blended together, phase separation, thickening, and/or flocculation can occur resulting in an uncoatable system; 2) the blended polymer system can be incompatible with other reagents which are often used in ink jet coating compositions; and 3) once the paper is coated and dried the incompatibility of the blends can result in a heterogeneous coating surface, which translates into varying degrees of image quality once printed.

A second approach cited in the prior art is to multi-coat paper to achieve the desired ink jet print qualities. For example, a multi-coated ink jet paper can contain a dye fixative layer where a cationic type polymer is typically the active agent, and a binder layer which often contains PVOH to bind the pigment.

The ink jet paper coating prior art discloses the use of various amine functional or cationic polymer and/or copolymer blends to impart ink or dye fixative properties to the finished ink jet papers.

U.S. applications Ser. No. 09/162,940 filed Sep. 29, 1998 and Ser. No. 09/119,563 filed Jul. 21, 1998 disclosed amine-modified PVOHs for ink jet paper coatings. Application '940 teaches PVOH graft polymerized with an ethylenically unsaturated monomer containing primary, secondary, tertiary or quaternary amine functionality. Application '563 teaches piperidone functionalized PVOH.

U.S. Pat. No. 5,270,103 discloses a receiver sheet which consists of a substrate and a coating containing a pigment and a binder. The binder comprises PVOH and an additional binder component; for example, a cationic polyamine, such as poly(2-hdyroxypropyl-1,1-N-dimethylammonium chloride) or poly(dimethyldiallyl-ammonium chloride), a cationic polyacrylamide, or a cationic polyethyleneimine. The receiver sheet is particularly useful for printing with aqueous based inks such as in ink jet printing systems.

JP 63049478 (abstract) discloses an ink jet paper coating composition by the homopolymerization of 2-(dimethylamino)ethyl methacrylate (DMAEMA) followed by quaternization by reacting with 3-chloro-2-hydroxypropyltrimethylammonium chloride to produce a cationic polymer. Paper is then coated with a blend consisting of this cationic polymer, PVOH, and silica to afford an ink jet recording sheet with good water and light resistance and good images.

JP 63160875 (abstract) discloses the use of an ink jet paper coating composition consisting of a methyl chloroacetate salt of a DMAEMA-methyl methacrylate-cyclohexylmethacrylate terpolymer blended with methyl cellulose and PVOH.

U.S. Pat. No. 4,944,988 discloses the use of and process for producing an ink jet recording paper coated with a composition containing silica, poly(sodium acrylate), PVOH, and a DMAEMA-vinyl acetate copolymer.

JP 06247036 (abstract) discloses the use of a PVOH, silica, and quaternized poly(ethylene imine) blend for coating ink jet paper.

JP 06297833 (abstract) discloses the use of a PVOH, pigment, and poly(ethylene imine) blend for coating ink jet paper to obtain sharp prints with uniform color.

JP 06143800 (abstract) discloses the double coating of paper with a blend of PVOH, silica, cationically modified PVOH, and quaternized poly(ethylene imine) to produce an ink jet recording sheet giving high density images and water resistance.

JP 01186372 discloses the coating of paper with a blend of PVOH, silica, and cationic poly(acrylamide) to produce an ink jet recording sheet giving high color density.

JP 01283182 (abstract) discloses the coating of paper with a blend of PVOH, silica, modified PVOH, and cationic poly(acrylamide) to produce a high quality ink jet recording sheet.

JP 63162276 (abstract) discloses the coating of paper with a blend of PVOH, silica, and cationically modified PVOH to produce an ink jet recording sheet giving good images, water resistance, and light resistance.

JP 59096987 (abstract) discloses an ink jet recording sheet which contains an alkylamine chloride and an alkylamine acetate.

Although there have been numerous references to alkylated polyamines, it has not been recognized that such materials have efficacy in ink jet paper coating compositions. The following patents and publications relate to alkylated polyethyleneamines and their applications:

U.S. Pat. No. 2,267,205 discloses detergent compositions containing compounds of the form $$X-NH-R-(NH-R)_n-NH-Y$$

in which R is an alkylene radical selected from the group consisting of ethylene and propylene radicals, n is 0, 1, or 2, and X is selected from the group consisting of hydrogen and lower alkyl radicals and Y is an alkyl radical having at least 7 and not more than 18 carbon atoms. The use of these materials in textile treatment and ore flotation is also disclosed.

U.S. Pat. No. 5,804,640 discloses water-based coating compositions which include a halogenated resin, a polyol, a surfactant, and an amine which can be of the form $$R_1-\underset{\underset{R_2}{|}}{N}-R_3-\underset{\underset{R_4}{|}}{N}-R_5-\underset{\underset{R_6}{|}}{N}-R_7$$

wherein R1–R7 are independently selected from H or straight or branched chain alkyl, hydroxyalkyl, or alkoxyalkyl groups of about 1 to about 20 carbon atoms.

U.S. Pat. No. 4,195,152 discloses MIBK and MIAK reductive alkylates of diethylenetriamine:

These materials are noted to be useful as curatives in high solids epoxy coatings because of their very low viscosity. Other suggested uses are in potting compositions, laminations, and adhesives.

Murata, Y.; Ueda, M. *J. Antibact. Antifung. Agents* 1989, 17 (8), 371–375 discloses trihydrochlorides of N,N"-dialkyldiethylenetriamines of the form $$R-NH\diagup\!\!\!\diagdown NH\diagup\!\!\!\diagdown NH-R$$

where R is a linear C8 or C10 alkyl group have been shown to have antimicrobial properties against dental plaque bacteria. This study showed that in vitro bactericidal activity tended to increase with the length of the N-substituted alkyl chain.

U.S. application Ser. No. 08/968,224 filed Nov. 12, 1997 discloses water-based compositions containing an alkylated polyamine compound of the following structure:

$$R-HN\diagup\!\!^{(CH_2)_m}\diagdown NH\diagup\!\!^{(CH_2)_n}\diagdown NH-R'$$

where m is 2–6, n is 2 or 3, and R and R' are C5 to C8 alkyl groups.

U.S. application Ser. No. 08/968,222 filed Nov. 12, 1997 discloses water-based compositions containing at least one alkylated polyamine compound of structures I and II:

$$RHN-[(CH_2)_nNH]_{p-(CH_2)_n}NHR \qquad \qquad I$$

where the R groups are independently hydrogen or C5 to C8 alkyl, provided that at least one R is not hydrogen; n is 2 to 6 and p is 2 to 8, and $$\begin{matrix} RHN(CH_2)_m \\ \diagdown \\ RHN(CH_2)_m \diagup \end{matrix} N-[(CH_2)_m NH]_t \!\!-\!\! \left[ (CH_2)_{\overline{m}} \underset{\underset{\underset{NHR}{(CH_2)_m}}{|}}{N} \right]_q \!\!-\!\! (CH_2)_{\overline{m}} [NH(CH_2)_m]_r \!-\! NHR \qquad II$$

where the R groups are independently hydrogen or C5 to C8 alkyl, provided at least one R is not hydrogen, m is 2 to 6, t is 0 to 3, q is 0 to 3, and r is 0 to 5.

SUMMARY OF THE INVENTION

This invention relates to improved ink jet paper coatings. The improvement resides in the use of a coating applied to a paper substrate which imparts high optical density images and good water resistance by incorporating into the coating composition a polymer having a plurality of pendent hydroxyl groups, preferably poly(vinyl alcohol) [PVOH], and at least one alkylated non-polymeric polyamine.

The alkylated non-polymeric polyamines can easily be blended into aqueous silica-containing ink jet coating compositions without unfavorable viscosities or flocculation to provide improved waterfastness.

There are several advantages to incorporating the above blend composition into ink jet paper coatings:

an ability to prepare high quality ink jet recording paper with a single coating of the composition;

an ability to produce high quality ink jet paper which, when printed, gives high optical density images with regard to monochrome black, composite black, and primary colors;

an ability to produce high quality ink jet paper which, when printed, yields waterfast images; and an ability to achieve fast ink dry times after printing onto ink jet paper coated with the above compositions.

In addition, there may be benefits derived from the ability of the alkylated non-polymeric polyamines to reduce dynamic surface tension while producing substantially no foam. Such a combination of properties could result in the ability to apply the coating more rapidly and to reduce the number of defects during the application of the coating to the paper.

In another embodiment of the invention a coated ink jet paper is prepared by:

(a) blending an aqueous solution of PVOH with an alkylated non-polymeric polyamine to afford an aqueous binder composition, such as an aqueous solution or dispersion;

(b) incorporating the aqueous binder composition into an aqueous pigment, preferably silica, slurry paper coating composition;

(c) coating a paper substrate with the aqueous binder-pigment slurry composition; and (d) drying the coated paper substrate.

DETAILED DESCRIPTION OF THE INVENTION

The ink jet recording paper according to the present invention has a coating applied thereon which contains a polymeric binder system comprising a polymer having a plurality of pendent hydroxyl groups on the polymer chain, such as PVOH, blended with one or more alkylated non-polymeric polyamines. One of the key findings of this invention is the superior performance achieved with alkylated non-polymeric polyamines compared to their non-alkylated counterparts. Another key finding is that amine functional or cationic polymer systems are not required to impart dye or ink fixative properties (i.e., waterfastness) to ink jet papers. Good waterfastness is achieved by simply incorporating alkylated non-polymeric polyamines into the coating composition.

By "non-polymeric polyamine" we mean a compound of up to 1000 molecular weight having at least two, preferably three or more, amine groups which may be primary, secondary or tertiary, i.e., a multi-amine functional compound.

Suitable alkylated non-polymeric polyamines are those non-polymeric polyamines which are N-alkylated sufficient to improve waterfastness, i.e., contain 5 to 75 eq %, preferably 25 to 50 eq % of the amine hydrogens replaced by a C3–C12 alkyl group. The alkyl groups may be the same or different. They may be linear or branched, and the point of attachment to the nitrogen of the polyamine may be on either an internal or terminal carbon. Preferred alkyl groups are derived from reductive alkylation reactions of a C5 to C8 aldehyde or ketone, especially those derived from reductive alkylation reactions of methyl isobutyl ketone or methyl isoamyl ketone. Specific examples of suitable C5 to C8 aldehydes and ketones include pentanal, 2-pentanone, 3-pentanone, methyl isopropyl ketone, hexanal, 2-hexanone, 3-hexanone, methyl tert-butyl ketone, ethyl isopropyl ketone, heptanal, 2-methylhexanal, 2-heptanone, 3heptanone, 4-heptanone, octanal, 2-octanone, 3-octanone, 4-octanone, 2-ethylhexanal, and so on.

Representative alkylated non-polymeric polyamines which can be employed as part of the ink jet paper coating composition, include hydrogenated adducts of dialkyl ketones with diethylenetriamine, triethylenetetramine, tetraethylenepentamine, tetraaminopropyldiaminobutane, and the like. Suitable dialkyl ketones, include methyl isobutyl ketone, methyl isoamyl ketone, and the like.

Examples of such alkylated non-polymeric polyamines include those taught in U.S. application Ser. No. 08/968,224 filed Nov. 12, 1997 which discloses alkylated polyamine compounds of the following structure 1:

                                                          1 where J is 2–6, preferably J is 2 or 3, K is 2 or 3, and the R groups are independently hydrogen or C5 to C8 alkyl, provided at least one R is not hydrogen, and U.S. application Ser. No. 08/968,222 filed Nov. 12, 1997 which discloses alkylated polyamine compounds of structure 2

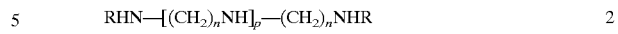
                                                          2 where the R groups are independently hydrogen or C5 to C8 alkyl, provided that at least one R is not hydrogen; n is 2 to 6 and p is 2 to 8, preferably R is C5 to C8 alkyl, n is 2 or 3 and p is 2 or 3, and structure 3

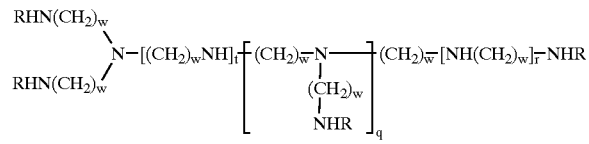
                                                          3 where the R groups are independently hydrogen or C5 to C8 alkyl, provided at least one R is not hydrogen, w is 2 to 6, t is 0 to 3, q is 0 to 3, and r is 0 to 5, preferably R is C5 to C8 alkyl, w is 2 or 3, t is 0 or 1, q is 0 to 2, and r is 0 to 3; the disclosures of both applications being hereby incorporated by reference.

Also suitable are alkylated polyamine compounds of structure 4

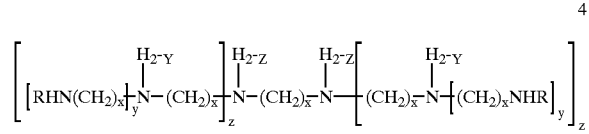
                                                          4 where the R groups are independently hydrogen or C5 to C8 alkyl, provided at least one R is not hydrogen, x is independently 2 to 6, y is 0 to 2, and z is 0 to 2; preferably the R groups are independently C5 to C8 alkyl x is independently 2 to 4, y is 1 or 2 and z is 1 or 2.

The alkylated polyamine compounds of structure 4 may be prepared by reacting appropriate di- and polyamino functional compounds with acrylonitrile such that some or all of the amine hydrogens are replaced by cyanoethyl groups. The nitrile functionalities are then reduced to primary amine functionalities by hydrogenation over a suitable catalyst, e.g., sponge nickel or sponge cobalt. The primary amine functionalities in turn are reductively alkylated with and aldehyde or ketone by hydrogenation with a suitable catalyst, e.g., platinum or palladium.

Diamine starting materials which are suitable for the above reaction sequence include 1,2-ethylenediamine, 1,3-propanediamine, 1,2-propanediamine, 1,4-butanediamine, 1,5-pentanediamine, 2-methyl-1,5-pentanediamine, 1,6-hexanediamine, and 1,2-cyclohexanediamine. Polyamino functional starting materials which are suitable for the same reaction sequence include diethylenetriamine, di-3-aminopropylamine, triethylenetetramine, tetraethylenepentamine, pentaethylenehexamine, N,N,N', N',-tetrakis(3-aminopropyl)-1,2-ethylenediamine, and N,N,N',N',-tetrakis(3-aminopropyl)-1,4-butanediamine.

The following reaction sequence shows alkylated non-polymeric polyamines via complete cyanoethylation of the starting amine.

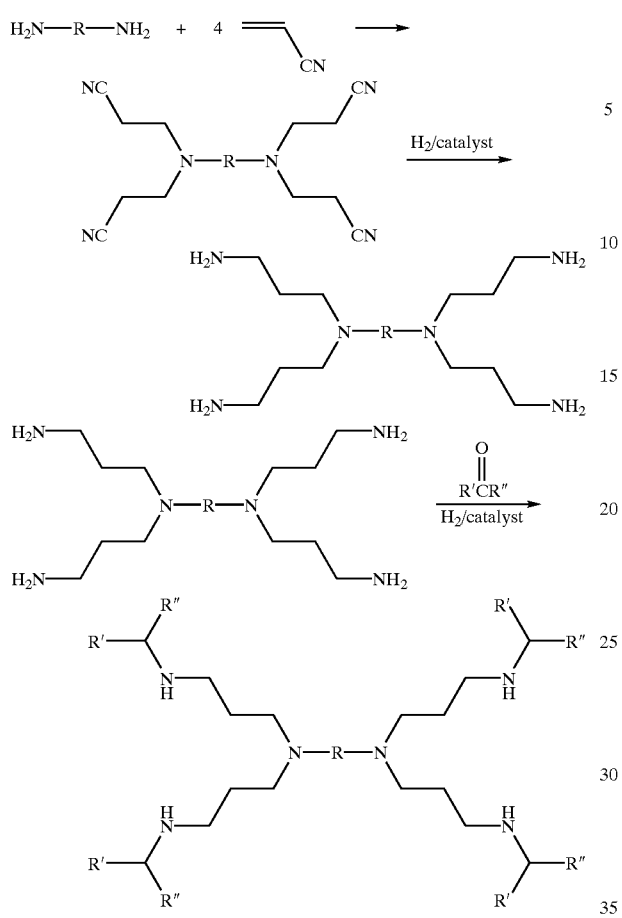

The following reaction sequence shows alkylated non-polymeric polyamines via incomplete cyanoethylation of starting amine.

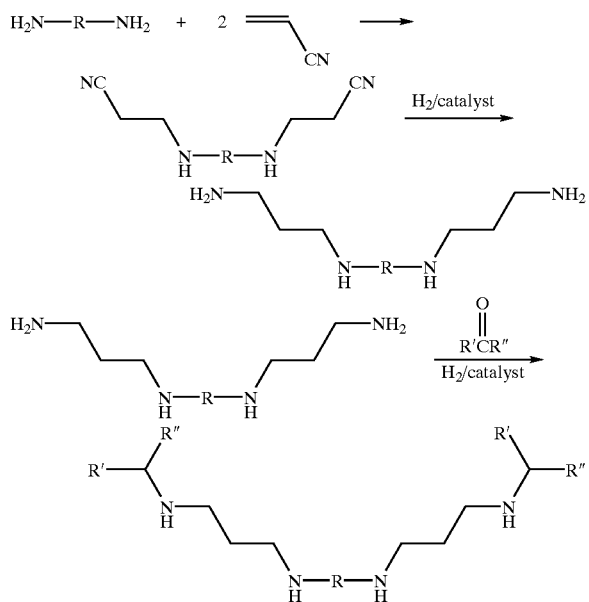

Specific examples of suitable alkylated non-polymeric polyamines, include the 4:1 hydrogenated adduct of methyl isobutyl ketone with tetraaminopropyldiaminobutane (TAPDAB/MIBK4), the 2:1 hydrogenated adduct of methyl isoamyl ketone with diethylenetriamine (DETA/MIAK2), and the 3:1 hydrogenated adduct of methylisobutyl ketone with the tris-(2-aminoethyl)amine (TAEA/MIBK3).

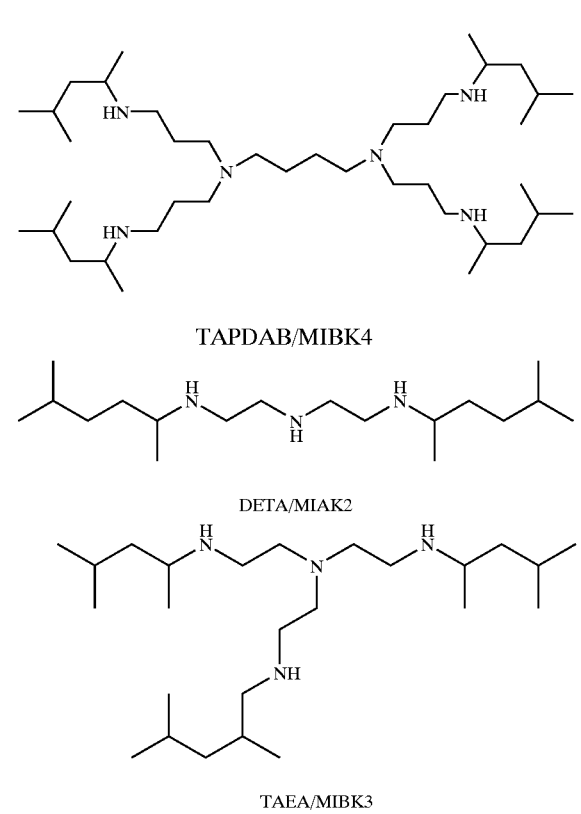

TAPDAB/MIBK4

DETA/MIAK2

TAEA/MIBK3

Polymers having a plurality of pendent hydroxyl groups can be formed by the polymerization of vinyl or acrylic esters in which the ester unit contains from 1 to 4 carbon atoms. The pendent ester groups, when hydrolyzed, form polymers containing pendent hydroxyl groups, A preferred class of polymers having a plurality of pendent hydroxyl groups are based upon hydrolyzed vinyl acetate polymers wherein vinyl acetate is polymerized as a homopolymer or in conjunction with other monomers to form copolymers and are known as PVOH or vinyl alcohol copolymers, respectively. Typically, the vinyl ester, specifically vinyl acetate, will comprise from 60 to 100 mole % of the copolymer, preferably at least 90 mole %, which hydrolyzed to the vinyl alcohol moiety.

The PVOH used in this invention, generally, has a weight average molecular weight (Mw) ranging from about 5,000 to 300,000, preferably 10,000 to 200,000. Alternatively, the PVOH can have a degree of polymerization (DPn) of from 100 to 5,000, preferably 200 to 3500. PVOH made commercially by the hydrolysis of poly(vinyl acetate) typically has a hydrolysis level ranging from about 85 to greater than 99 mole %. For this invention, the level of hydrolysis can range from 50 to greater than 99 mole %, preferably 85 to 98 mole %. Mixed PVOH grades, using combinations of PVOHs varying in molecular weight and hydrolysis level, can also be employed in the present invention.

A variety of monomers may be copolymerized with a vinyl ester to produce copolymers containing vinyl alcohol units. Monomers which can be polymerized with the vinyl ester, preferably vinyl acetate, include ethylene, unsaturated acids such as maleic, acrylic and methacrylic acid, and esters, such as the C1 to C12, preferably C1 to C6 alkyl esters of acrylic or methacrylic acid. In many instances, these polymers can be hydrolyzed to produce different grades of PVOH including, for example, hydrolyzing only the vinyl ester and leaving the acrylic ester functionality intact. Other monomers having from 2 to 12 carbon atoms such as alkyl maleates (e.g., dibutyl maleate and the like) may be polymerized as desired with vinyl acetate to control hydrophilic and hydrophobic content. Vinyl alcohol copolymers which can be utilized in this invention are soluble in water.

Table 1 sets forth the operative and preferred ranges regarding the use of alkylated non-polymeric polyamine blends with PVOH as the binder system:

TABLE 1

|  | Operative Range | Preferred Range |
| --- | --- | --- |
| PVOH (Mw) | 5,000–300,000 | 10,000–200,000 |
| Mole % hydrolysis | 50–>99 | 85–98 |
| Wt % alkylated polyamine relative to PVOH | 0.5–70 | 5–30 |
| Wt % binder in ink jet coating | 5–90 | 10–50 |
| Wt % pigment in ink jet coating | 10–95 | 50–90 |
| ink jet coating pH | 3–10 | 4–8 |

Ink jet coating compositions typically contain pigment such as silica aluminum silicate, clay, talc, calcium carbonate, magnesium silicate, and the like, desirably silica having a surface area of 50 to 700 $m^2/g$ and possibly a small amount of one of the other mineral pigments. The silica pigment is typically incorporated in the ink jet coating composition in amounts ranging from about 10 to about 95 wt %, preferably 50 to 90 wt %, (solids basis). The polymeric binder (PVOH and polyamine) level can range from 5 to 90 wt % of the ink jet composition (solids basis), preferably 10 to 50 wt %.

The level of pigment and binder depend on the type of coater used in the preparation of the ink jet paper. For example a puddle size press application would use a low wt % of pigment relative to the binder due to viscosity limitations in comparison to an air knife coater where pigment to binder ratio would be greater. Ink jet compositions can also contain conventional additives such as defoamers, surface active agents, dyes, ultraviolet absorbents, pigment dispersants, mold inhibitors, thickeners and water-resisting agents.

The ink jet composition is usually applied to the paper surface in amounts ranging from about 2 to 20 $g/m^2$, preferably, 3 to 15 $g/m^2$. Coat weight varies depending on the type of coating applicator. For example a puddle size press may only apply a coat weight of 2 to 4 $g/m^2$, whereas an air knife could provide up to 10 $g/m^2$.

Although any kind of paper can be used for application of ink jet coatings of this invention, uncoated wood-free paper is preferred.

Not intending to be bound by theory, it is believed the amine groups in the alkylated non-polymeric polyamine provide a cationic charge on the paper surface which reacts with the anionic sulfonic acid groups of the direct or acid dye of the ink jet inks to form an insoluble salt. As such, the inks become waterfast on the paper surface. Pigment binding strength is also improved with the use of alkylated non-polymeric polyamines due to the strong absorption of the amines with the silanol groups on the silica pigment.

EXAMPLE 1

TAEA/MIBK3

Tris(2-aminoethyl)amine (0.5 mole) (TAEA), methyl isobutyl ketone (1.68 mole) (MIBK) and 10% Pd/C (4 wt % of total charge) were charged to a one liter stainless steel autoclave. The reactor was sealed and purged with nitrogen then hydrogen. The contents of the reactor were heated to 80° C. under 7 bar (100 psig) hydrogen The hydrogen pressure was increased to 55 bar (800 psig) and maintained throughout the reaction (24 hours) by the admission of hydrogen from a 1 gallon (3.8 L) ballast on demand by a dome regulator. The crude product was concentrated in vacuo and then distilled at 160–166° C. at 1.0 millibar (0.8 torr) to give 173.0 g as a clear colorless liquid.

EXAMPLE 2

TAPDAB/MIBK4

Tetraaminopropyldiaminobutane (0.41 mole, 65% solution in isopropanol) (TAPDAB), MIBK (1.72 mole) and 10% Pd/C (3 wt % of total charge) were charged to a one liter stainless steel autoclave and reacted as in Example 1 for 24 hours. The crude product was concentrated in vacuo and then heated to about 175° C. at 1.3 millibar for 20 minutes to remove the remaining water and volatile organics to a clear colorless liquid with 0.06 wt % water by Karl Fischer titration.

EXAMPLE 3

DETA/MIAK2

Diethylenetriamine (1.5 mole) (DETA), methyl isoamyl ketone (3.2 mole) (MIAK) and 10% Pd/C (2.4 wt % of total charge) were charged to a one liter stainless steel autoclave and reacted as in Example 1 for 5 hours. The reactor contents were analyzed by GC/FID and found to be 92.4 area % dialkylated diethylenetriamine. The product was purified by distillation at 155–157° C., 2.7 millibar (2 Torr).

EXAMPLE 4

A blend of PVOH and alkylated non-polymeric polyamines was prepared as follows: Airvol® 523 PVOH (21 g, DPn~1200, 88 mole % hydrolyzed) was dissolved in water (127 g) to provide a 14.1% solution by stirring at 90° C. for 30 minutes. To this cooled PVOH solution was added the 4:1 hydrogenated adduct of methyl isobutyl ketone with tetraaminopropyldiaminobutane (2.4 g, TAPDAB/MIBK4) with stirring. The blend pH was then adjusted between 6 and 8 with acetic acid. The resulting homogeneous aqueous polymer blend was used without further purification in formulating the paper coatings. The other amine/PVOH blends of Table 2 were similarly prepared.

EXAMPLE 5

Ink Jet Coating Preparation

Sheets of uncoated base paper were coated for the purpose of evaluating ink jet optical density for several colors and waterfastness. A paper coating dispersion was prepared by mixing 800 parts water, 100 parts silica pigment, and 40 parts (solids basis) of the blend prepared in Example 4. In preparing the coatings, a dispersion of silica pigment in water was prepared first followed by the addition of the PVOH blend with alkylated non-polymeric polyamines (e.g., the blend prepared in Example 4) to this dispersion under high shear. The resulting dispersion was coated onto uncoated wood free paper having a basis weight of 40 g/m² at a coat weight of 7–8 g/m², using a Meyer Rod draw down bar. After coating and drying at 250° F. (121° C.) for 60 seconds, the sheets were printed with a Hewlett Packard 560 ink jet printer using an HP test pattern distributed by Hewlett Packard for the purpose of testing ink jet paper media. After printing, the samples were measured for optical density using a Tobias IQ 200 Reflection Densitometer. The waterfastness test was performed by first measuring the monochrome black ink density after printing. The printed area was then immersed in distilled water for 30 seconds with slight agitation and dried on a hot plate under tension. The optical density was then measured again.

Table 2 shows the ink-jet data for PVOH/alkylated amine blends, i.e., the binder system, in an ink jet coating composition of 15 wt % solids comprising 100 wt parts silica and 40 wt parts binder. The indicated amine was blended with aqueous AIRVOL 523 PVOH (14.1 wt % aq solution) at the indicated dry weight ratio of amine:PVOH. The aqueous blend pH was adjusted to 7–8 with acetic acid, Waterfastness was measured as the % loss in monochrome black ink optical density after soaking the printed paper in water for 30 seconds.

TABLE 2

| Binder System | Ink Optical Density and Waterfastness | | | | | |
|---|---|---|---|---|---|---|
| Wt % Amine Blended with AIRVOL ® 523 | Mono-black | Magenta | Yellow | Cyan | Comp. black | Waterfastness |
| 10% DETA | 1.00 | 0.81 | 0.55 | 1.09 | 0.67 | −39.2% |
| 10% TBA | 1.08 | 0.75 | 0.53 | 1.01 | 0.70 | −47.7% |
| 10% TETA | 1.09 | 0.93 | 0.66 | 1.26 | 0.79 | −43.8% |
| 10% TEPA | 1.08 | 0.82 | 0.61 | 1.08 | 0.79 | −29.1% |
| 10% octylamine | 1.23 | 0.86 | 0.62 | 1.15 | 0.81 | −47.9% |
| 10% dodecylamine | 1.24 | 0.76 | 0.58 | 0.98 | 0.77 | −24.4% |
| 10% TAPDAB/MIBK4 | 1.12 | 0.81 | 0.57 | 1.10 | 0.91 | −3.6% |
| 15% TAPDAB/MIBK4 | 1.11 | 0.72 | 0.50 | 0.96 | 0.92 | 0 |
| 20% TAPDAB/MIBK4 | 1.12 | 0.82 | 0.53 | 1.06 | 0.93 | 0 |
| 10% DETA/MIAK2 | 1.22 | 0.74 | 0.50 | 0.90 | 0.84 | −15.1% |
| 20% DETA/MIAK2 | 1.23 | 0.73 | 0.52 | 0.92 | 0.81 | −5.7% |
| 10% TAEA/MIBK3 | 1.20 | 0.85 | 0.62 | 1.02 | 0.99 | −3.1% |
| 10% TETA/MIBK2 | 1.16 | 0.77 | 0.54 | 0.94 | 0.85 | −18.5% |
| Airvol ® 523 - no amine | 1.16 | 0.87 | 0.61 | 1.12 | 0.82 | −51.7% |

Table 2 compares the ink optical density and water resistance of printed images on ink jet papers coated with the blends described in this invention. Comparative amines, such as DETA and TETA, actually degrade the print quality and offer insignificant waterfastness improvement when incorporated into an ink jet paper coating composition compared to a coating containing only silica and PVOH. However, upon alkylation of these amines, such as DETA/MIAK2, TAEA/MIBK3, and especially TAPDAB/MIBK4, there are significant improvements in waterfastness, in some instances even complete waterfastness is achieved, as well as very good ink optical densities.

Statement of Industrial Application

The present invention provides coating compositions for making ink jet recording paper.

We claim:

1. In an aqueous pigmented coating composition for ink jet recording paper containing 10–95 wt %, solids basis, of a mineral pigment which is silica, aluminum silicate, clay, talc, calcium carbonate, magnesium silicate, titanium dioxide or aluminum hydrate and 5–90 wt %, solids basis, of a polymeric binder in an aqueous medium, the improvement which comprises the polymeric binder comprising a polyvinyl alcohol and an alkylated non-polymeric polyamine, whereby the composition is suitable as a coating for ink jet recording paper.

2. The aqueous coating composition of claim 1 wherein the mineral pigment is silica and the alkylated non-polymeric polyamine is selected from the group consisting of alkylated polyamine compounds of structure 1:

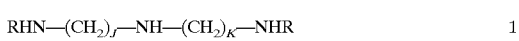

where J is 2–6, K is 2 or 3, and the R groups are independently hydrogen or C5 to C8 alkyl, provided that at least one R is not hydrogen;

alkylated polyamine compounds of structure 2:

where the R groups are independently hydrogen or C5 to C8 alkyl, provided that at least one R is not hydrogen; n is 2 to 6 and p is 2 to 8;

alkylated polyamine compounds of structure 3

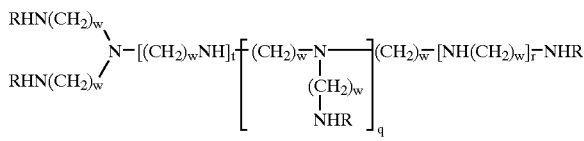

where the R groups are independently hydrogen or C5 to C8 alkyl, provided that at least one R is not hydrogen, w is 2 to 6, t is 0 to 3, q is 0 to 3, and r is 0 to 5; and alkylated polyamine compounds of structure 4

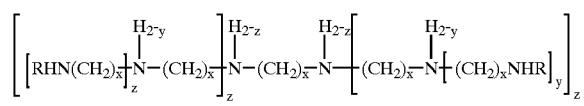

where the R groups are independently hydrogen or C5 to C8 alkyl, provided that at least one R is not hydrogen, x is independently 2 to 6, y is 0 to 2, and z is 0 to 2, and combinations thereof.

3. The aqueous coating composition of claim 2 in which the alkylated non-polymeric polyamine is selected from the group consisting of the 4:1 hydrogenated adduct of methyl isobutyl ketone with tetraaminopropyldiaminobutane (TAPDAB/MIBK4), the 2:1 hydrogenated adduct of methyl isoamyl ketone with diethylenetriamine (DETA/MIAK2), and the 3:1 hydrogenated adduct of methylisobutyl ketone with the tris-(2-aminoethyl)amine (TAEA/MIBK3).

4. The aqueous coating composition of claim 2 wherein the polyvinyl alcohol has a weight average molecular weight from 5,000 to 300,000 and a degree of hydrolysis from 50 to greater than 99 mole %.

5. The aqueous coating composition of claim 2 wherein the polyvinyl alcohol has a weight average molecular weight from 10,000 to 200,000 and a degree of hydrolysis from 85 to 98 mole %.

6. The aqueous coating composition of claim 2 wherein the polymeric binder is present in an amount of 10 to 50 wt % and the silica is present in an amount of 50 to 90 wt %, on a solids basis.

7. An aqueous pigmented coating composition for ink jet recording paper consisting essentially of, in water, 50–90 wt %, solids basis, silica pigment and 10–50 wt %, solids basis, polymeric binder which comprises polyvinyl alcohol having a weight average molecular weight from 10,000 to 200,000 and a degree of hydrolysis from 85 is to 98 mole %, and 5–30 wt %, based on polyvinyl alcohol, of an alkylated non-polymeric polyamine selected from the group consisting of alkylated polyamine compounds of structure 1:

      1 where J is 2–6, K is 2 or 3, and the R groups are independently hydrogen or C5 to C8 alkyl, provided at least one R is not hydrogen;

alkylated polyamine compounds of structure 2:

      2 where the R groups are independently hydrogen or C5 to C8 alkyl, provided that at least one R is not hydrogen; n is 2 to 6 and p is 2 to 8;

alkylated polyamine compounds of structure 3

3

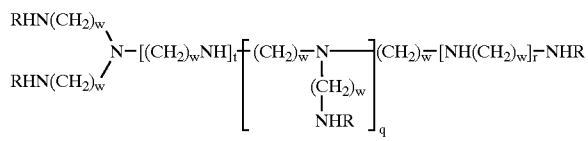

where the R groups are independently hydrogen or C5 to C8 alkyl, provided at least one R is not hydrogen, w is 2 to 6, t is 0 to 3, q is 0 to 3, and r is 0 to 5; and alkylated polyamine compounds of structure 4

4

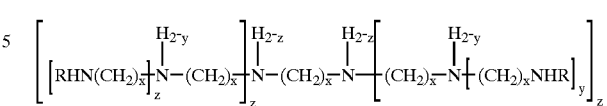

where the R groups are independently hydrogen or C5 to C8 alkyl, provided at least one R is not hydrogen, x is independently 2 to 6, y is 0 to 2, and z is 0 to 2, and combinations thereof, whereby the composition is suitable as a coating for ink jet recording paper.

8. The aqueous coating composition of claim 7 in which the alkylated non-polymeric polyamine is an alkylated polyamine compound of structure 1:

      1 where J is 2 or 3, K is 2 or 3, and the R groups are C5 to C8 alkyl.

9. The aqueous coating composition of claim 7 in which the alkylated non-polymeric polyamine is an alkylated polyamine compound of structure 2

      2 where the R groups are independently C5 to C8 alkyl, n is 2 or 3 and p is 2 or 3.

10. The aqueous coating composition of claim 7 in which the alkylated non-polymeric polyamine is an alkylated polyamine compound of structure 3

3

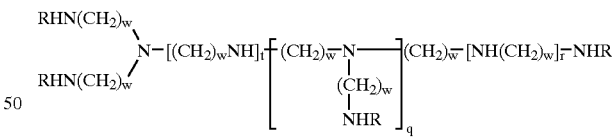

where the R groups are independently C5 to C8 alkyl, w is 2 or 3, t is 0 or 1, q is 0 to 2, and r is 0 to 3.

11. The aqueous coating composition of claim 7 in which the alkylated non-polymeric polyamine is an alkylated polyamine compound of structure 4

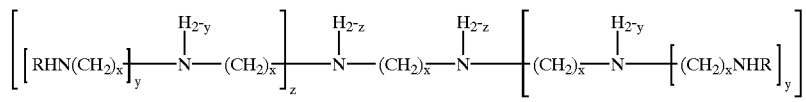

where the R groups are independently C5 to C8 alkyl, x is independently 2 to 4, y is 1 or 2, and z is 1 or 2.

12. The aqueous coating composition of claim 7 in which the alkylated non-polymeric polyamine is selected from the group consisting of the 4:1 hydrogenated adduct of methyl isobutyl ketone with tetraaminopropyldiaminobutane (TAPDAB/MIBK4), the 2:1 hydrogenated adduct of methyl isoamyl ketone with diethylenetriamine (DETA/MIAK2), and the 3:1 hydrogenated adduct of methylisobutyl ketone with the tris-(2-aminoethyl)amine (TAEA/MIBK3).

13. The aqueous coating composition of claim 7 which also comprises one or more additives selected from the group consisting of defoamers, surface active agents, dyes, ultraviolet absorbents, pigment dispersants, mold inhibitors, thickeners and water-resisting agents.

* * * * *

UNITED STATES PATENT AND TRADEMARK OFFICE
CERTIFICATE OF CORRECTION

PATENT NO. : 6,458,876 B1
DATED : October 1, 2002
INVENTOR(S) : John Joseph Rabasco et al.

It is certified that error appears in the above-identified patent and that said Letters Patent is hereby corrected as shown below:

Column 14,
Line 61, delete the formula at the end of Column 14

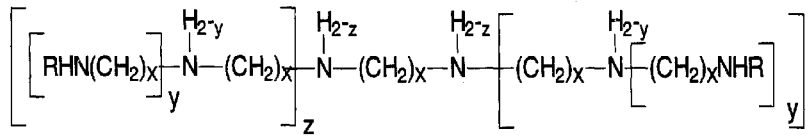

Replace with:

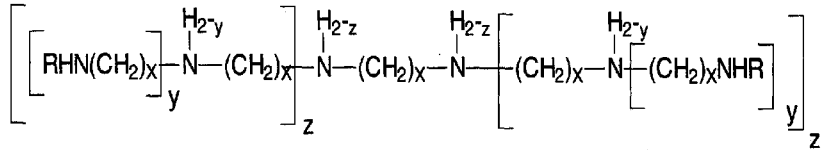

Signed and Sealed this

Twenty-eighth Day of January, 2003

JAMES E. ROGAN
*Director of the United States Patent and Trademark Office*